US012725694B2

(12) United States Patent
André et al.

(10) Patent No.: US 12,725,694 B2
(45) Date of Patent: Sep. 1, 2026

(54) SYSTEMS AND METHODS FOR REAL-TIME PROCESSING OF MEDICAL IMAGING DATA UTILIZING A SINGLE INSTRUCTION MULTIPLE DATA PROCESSOR

(71) Applicant: Stryker Corporation, Kalamazoo, MI (US)

(72) Inventors: Marc André, Spiegel b. Bern (CH); Benjamin Hyman Feingold, San Francisco, CA (US); Jessie Ying Chi Ng, Vancouver (CA); Rohit Subramanian, San Jose, CA (US)

(73) Assignee: Stryker Corporation, Portage, MI (US)

( * ) Notice: Subject to any disclaimer, the term of this patent is extended or adjusted under 35 U.S.C. 154(b) by 51 days.

(21) Appl. No.: 18/396,673

(22) Filed: Dec. 26, 2023

(65) Prior Publication Data

US 2024/0212831 A1 Jun. 27, 2024

Related U.S. Application Data

(60) Provisional application No. 63/477,374, filed on Dec. 27, 2022.

(51) Int. Cl.
*G16H 30/40* (2018.01)
*G06F 9/38* (2018.01)

(52) U.S. Cl.
CPC ........... *G16H 30/40* (2018.01); *G06F 9/3887* (2013.01)

(58) Field of Classification Search
CPC .............................. G16H 30/40; G06F 9/3887
See application file for complete search history.

(56) References Cited

U.S. PATENT DOCUMENTS 3,611,300 A * 10/1971 Aldrich ............... G06F 15/8007 712/34
7,254,283 B1 * 8/2007 Nishigaki ................. G06T 1/20 382/284

(Continued)

FOREIGN PATENT DOCUMENTS

EP 3666164 A1 6/2020
KR 10-2020-0076150 A 6/2020

(Continued)

OTHER PUBLICATIONS

Glatz. (Oct. 27, 2014). "Real-time intra-operative and endoscopic molecular fluorescence imaging," located at http://medatum.ub.tum.de/doc/1230920/1230920.pdf. (175 pages).

(Continued)

*Primary Examiner* — Michael Tomaszewski
(74) *Attorney, Agent, or Firm* — Morrison & Foerster LLP

(57) ABSTRACT

A system for processing and displaying medical imaging data onto an electronic display is configured to: access a plurality of data portions corresponding to a frame of the one or more video frames stored in memory; process the plurality of data portions using a single instruction multiple data (SIMD) processing architecture such that each data portion of the plurality of data portions is separately processed in parallel using one or more common instructions; and transmit the processed plurality of data portions to an electronic display; and a second processor, wherein the second processor is communicatively coupled to the first processor, and wherein the second processor is configured to coordinate one or more operations of the first processor.

40 Claims, 11 Drawing Sheets

(56) References Cited

U.S. PATENT DOCUMENTS 8,266,333 B1 * 9/2012 Wade .................. H04N 19/436
710/36
9,980,629 B2 * 5/2018 King .................. A61B 1/00057
10,058,237 B2 * 8/2018 Ichiki ............... A61B 1/000095
10,440,241 B2 * 10/2019 Yamane .................... G06T 1/20
2004/0086177 A1 * 5/2004 Zhang .................. H04N 25/134
382/167
2004/0223003 A1 * 11/2004 Heirich ................. G06T 15/005
345/629
2008/0181471 A1 * 7/2008 Chung ...................... G06T 1/00
382/128
2008/0181472 A1 * 7/2008 Doi ........................ G16H 30/40
382/128
2010/0186017 A1 * 7/2010 Eeratta .................... G06F 9/505
345/522
2010/0310143 A1 * 12/2010 Rao .......................... G06T 5/20
382/131
2014/0055465 A1 * 2/2014 Diercks ................. G06T 15/005
345/506
2018/0293699 A1 * 10/2018 Venkatesh ........... G06F 9/30145
2020/0135330 A1 4/2020 Sugie
2020/0177870 A1 * 6/2020 Tadi ........................ G06F 3/011
2020/0184640 A1 * 6/2020 Mahadik ................... G06T 7/12
2020/0303060 A1 * 9/2020 Haemel .................. G16H 40/63
2021/0218898 A1 * 7/2021 Moon ................ H04N 23/6812
2021/0334975 A1 * 10/2021 Yang ...................... G06N 3/084
2021/0374947 A1 * 12/2021 Shin ....................... G06N 3/094
2022/0000567 A1 1/2022 Wade
2022/0253980 A1 * 8/2022 Wang .................... G06T 7/0002
2022/0343822 A1 * 10/2022 Bogdanowicz ...... G09G 3/2003
2023/0077690 A1 * 3/2023 Tsutaoka .............. G06V 10/774
382/128
2024/0212831 A1 * 6/2024 André .................... G16H 30/40

FOREIGN PATENT DOCUMENTS

WO 2018/203473 A1 11/2018
WO 2019/003911 A1 1/2019
WO WO-2019051227 A1 * 3/2019 ............. G16H 50/30
WO 2019/103215 A1 5/2019

OTHER PUBLICATIONS

International Preliminary Report on Patentability dated Jul. 1, 2025, directed to International Application No. PCT/US2023/085939; 10 pages.

International Search Report and Written Opinion mailed Apr. 2, 2024, directed to International Application No. PCT/US2023/085939; 15 pages.

* cited by examiner

SYSTEMS AND METHODS FOR REAL-TIME PROCESSING OF MEDICAL IMAGING DATA UTILIZING A SINGLE INSTRUCTION MULTIPLE DATA PROCESSOR

CROSS-REFERENCE TO RELATED APPLICATIONS

This application claims the benefit of U.S. Provisional Application No. 63/477,374 filed Dec. 27, 2022, the entire contents of which are incorporated herein by reference.

FIELD

This disclosure relates to computing and processing system architectures for real-time processing and displaying of medical imaging data (such as endoscopy and/or fluorescence imaging and/or open field surgical imaging) that provide robust processing capabilities while also minimizing system latency to ensure that any processing does not lead to significant time lag between the collection of the imaging data and the display of the data.

BACKGROUND

Medical imaging involves the use of a high-definition camera often coupled to an endoscope inserted into a patient to provide a surgeon with a clear and precise view within the body. In many instances, the video data collected at the camera will be transmitted to a display device that will render the video data collected onto a display so that the surgeon can visualize the area of the body that is being viewed by the camera. In many instances, such as in endoscopic imaging, the camera can serve as the eyes of the surgeon during the surgery since the camera may provide the only view of an internal area of the patient. Because of this critical function served by the medical imaging device, the computing/processing system that transfers the data collected by the camera to a display for viewing by a surgeon will be required to process imaging data in a manner with little to no latency. In other words, any significant delay between when an event occurs on camera and when that event is displayed to the surgeon could lead to an unsafe operating environment. If the latency of such a system is significant, the actions the surgeon is taking during the surgery may not be reflected in what the surgeon is seeing on the screen.

Capturing imaging data using a camera can present an opportunity for post-capture processing that can improve the way in which the imaging data is displayed on the screen. The imaging data is converted into a digital representation which can be processed and even manipulated to improve the appearance of the data before it is displayed. For instance, various image processing algorithms can be employed to improve the resolution of the camera data before the data is ultimately rendered on a display. Furthermore, machine learning algorithms can be used to for instance identify objects or artifacts in the imaging data, segment image data, and augment the imaging data. However, current processing architectures for medical imaging data do not allow for the full use of available image processing techniques since employing such techniques on existing architectures may often lead to unacceptable lag between the collection of imaging data and its display.

In one or more examples, medical imaging data processors consist of a collection of Field Programmable Gate Arrays (FPGAs), Application Specific Integrated Circuits (ASICs), and generalized central processing units (CPUs) connected to memory that collectively are configured to receive imaging data from the camera and render the data on a display for viewing by the surgeon. These medical imaging data processing architectures discussed above often use multiple instruction multiple data (MIMD) processing techniques to affect any algorithms or processing that are performed on acquired medical imaging data. However, MIMD techniques may not be compatible or practical to use with some image processing techniques as using MIMD could lead to unacceptable latency in the system, and/or significantly slow and burdensome algorithm development. As an example, the development of an image rotation algorithm for an auto-horizon application can take many months of development work due to the need to tailor the algorithm to an MIMD processing architecture. A processing architecture that can increase the real-time processing capabilities of medical imaging data while minimizing image latency can represent a significant improvement over current medical image processing systems.

SUMMARY

According to an aspect, video data taken from an endoscopic or other medical imaging device can be transmitted from the device to a display for rendering the data on a screen. In one or more examples, the data can be transmitted from the device to the display via a computing system configured to process the imaging data using one or more processing algorithms. In one or more examples, the system can include a single instruction multiple data (SIMD) processor that is configured to process multiple data portions of the digital image data using a single instruction. In one or more examples, the system can include a CPU which can be configured to coordinate one or more operations of the SIMD processor. Optionally, the system can include an integrated circuit that is configured to received one or more frames of imaging data collected from a medical imaging device, temporarily store the received data, and transfer the data to a memory that is coupled to the SIMD process once an entire frame of data has been collected. In one or more examples, the SIMD processor can output the data directly to the display using an HDMI connection or other interface format. In one or more examples, the SIMD processor can output processed data to the integrated circuit, which can then interface with the display to transmit the data. In one or more examples, the integrated circuit can receive data from the imaging device and output data to the display using direct memory access (DMA) transfer. In one or more examples, the SIMD processor can be communicatively coupled to an image signal processor. In one or more examples, the SIMD processor can be utilized to perform certain algorithms, while other algorithms can be performed on the image signal processor or other processing components that are part of the system.

According to an aspect, a system for processing and displaying medical imaging data onto an electronic display includes: a memory, wherein the memory is configured to be communicatively coupled to a medical imaging device, and wherein the memory is configured to: receive one or more frames of video data from the medical imaging device, wherein each frame of the one or more frames comprises a plurality of data portions, and store the plurality of data portions of each frame of the received video data in one or more storage mediums of the memory; a first processor configured to: access the plurality of data portions corresponding to a frame of the one or more frames from the memory, process the plurality of data portions using a single instruction multiple data (SIMD) processing architecture such that each data portion of the plurality of data portions is separately processed in parallel using one or more common instructions, and transmit the processed plurality of data portions to an electronic display; and a second processor communicatively coupled to the first processor configured to coordinate one or more operations of the first processor.

The system may include an integrated circuit configured to: receive the one or more frames of video data from the medical imaging device; convert each frame of the one or more frames of video data into a plurality of packets, wherein each packet includes a portion of the frame; and transfer the plurality of packets associated with each frame to the memory.

The plurality of packets may include Peripheral Component Interconnect Express (PCIe) packets. Transferring the plurality of packets to the memory may include performing a direct memory access (DMA) transfer. The DMA transfer may be controlled by the integrated circuit. The DMA transfer may be controlled by the second processor.

The integrated circuit may be configured to: determine that one or more portions of the one or more frames has been received from the medical imaging device; and transmit a signal to the second processor when a determination has been made that the one or more portions of the one or more frames has been received from the medical imaging device. The second processor may be configured to: receive the signal from the integrated circuit indicating that a complete frame of the one or more frames has been received from the medical imaging device; and cause the first processor to initiate processing the plurality of data portions upon receiving the signal from the integrated circuit indicating that a complete frame of the one or more frames has been received from the medical imaging device. The first processor may be configured to: receive the signal from the integrated circuit indicating that a complete frame of the one or more frames has been received from the medical imaging device; and initiate processing the plurality of data portions upon receiving the signal from the integrated circuit indicating that a complete frame of the one or more frames has been received from the medical imaging device.

The integrated circuit may be configured to perform one or more image processing algorithms on the received one or more frames of video data.

The integrated circuit may be configured to receive one or more processed images from the first processor and is configured to perform one or more image processing algorithms on the received one or more processed images.

The integrated circuit may be configured to receive one or more processed images from the first processor using a direct memory access (DMA) transfer. The integrated circuit may include one or more output ports and is configured to output the received one or more processed images to the electronic display using the one or more output ports. The one or more output ports may include high-definition multimedia interface (HDMI) output ports. The one or more output ports may include DisplayPorts compatible output ports. The one or more output ports may include Serial Digital Interface (SDI) output ports.

The system may include a multiplexer that comprises: a first input communicatively coupled to the output port of the integrated circuit, a second input of the multiplexer communicatively coupled to an output port of the first processor, and an output port communicatively coupled to the electronic display, and the multiplexer may be configured to select the first input or the second input to be transmitted to the electronic display using the output port based on one or more control signals received from the integrated circuit.

The integrated circuit may be configured to: receive an image from the first processor to be overlaid on the one more received processed images from the first processor; superimpose the received image onto the one or more received processed images to generate a composite image; and transmit the composite image to the electronic display.

The integrated circuit may be a field programmable gate array (FPGA).

The integrated circuit may be configured to be communicatively coupled to a light source, and wherein the integrated circuit is configured to operate the light source.

The integrated circuit may be configured to determine if the first or second processor has failed and, if it is determined that the first or second processor has failed: perform one or more image processing algorithms on the received one or more frames of video data to generate one or more processed frames of video data; and transmit the one or more processed frames of video data to the electronic display.

The memory may be configured to receive the one or more frames of video data in a mobile industry processor interface (MIPI) camera serial interface (format).

The system may include a third processor configured to perform one or more image signal processing algorithms on the received one or more frames of video data. The one or more image signal processing algorithms may include a de-mosaic algorithm. The one or more image signal processing algorithms may include a noise reduction algorithm.

Processing the plurality of data portions may include applying one or more image signal processing algorithms selected from the group consisting of: Pixel defect correction, color leakage correction, de-mosaic, spatial and temporal noise reduction filters, sharpening filters, color space conversion, image stabilization, overlay of multiple image sensors, image augmentation, gamma correction, dewarping, and distortion correction.

The second processor may be configured to execute an operating system configured to manage operation of the first processor.

The first processor may be a graphics processing unit (GPU).

The first processor may be configured to be communicatively coupled to a light source, and wherein the first processor is configured to operate the light source.

The second processor may be configured to be communicatively coupled to a light source, and wherein the second processor is configured to operate the light source.

Processing the plurality of data portions may include applying one or more artificial intelligence applications to the plurality of data portions.

The first processor may include one or more tensor cores configured to perform matrix operations. The one or more tensor cores may be configured to apply the one or more artificial intelligence applications to the plurality of data portions.

The memory may be a buffer that is part of the first processor.

The memory may be a system memory shared by the first and second processors.

The first processor may be configured to perform one or more iterative algorithms on the plurality of data portions, wherein performing an iterative algorithm may include: applying a first common instruction to each data portion of the plurality of data portions to generate a plurality of first processed data portions; storing each data portion of the plurality of first processed data portions in the memory; and applying a second common instruction to each data portion of the plurality of first processed data portions stored in the memory to generate a plurality of second processed data portions.

The first processor may be configured to perform video encoding on the received one or more frames of video data.

Performing video encoding on the received one or more frames may include applying H.264 encoding on the received one or more frames of video data.

The first processor may be configured to perform one or more image processing algorithms on the received one or more frames of video data selected from the group consisting of pixel defect correction, color leakage correction, demosaicing, spatial filtering, temporal noise filtering, sharpening filtering, color space conversion, image stabilization, image augmentation, gamma correction, dewarping, image compression, image decompression, and distortion correction.

The electronic display and the medical imaging device may be operated using a common clock signal generated by the system.

According to an aspect, a method for processing and displaying medical imaging data onto an electronic display includes accessing, by a first processor, a plurality of data portions stored in a memory, the plurality of data portions corresponding to a frame of one or more frames of video data from a medical imaging device; processing, by the first processor, the plurality of data portions using a single instruction multiple data (SIMD) processing architecture such that each data portion of the plurality of data portions is separately processed in parallel using one or more common instructions; transmitting, by the first processor, the processed plurality of data portions to an electronic display; and coordinating, by a second processor, one or more operations of the first processor.

The method may include, at an integrated circuit of the computing system: receiving the one or more frames of video data from the medical imaging device; converting each frame of the one or more frames of video data into a plurality of packets, wherein each packet includes a portion of the frame; and transferring the plurality of packets associated with each frame to the memory. The plurality of packets may be Peripheral Component Interconnect Express (PCIe) packets. Transferring the plurality of packets to the memory may include performing a direct memory access (DMA) transfer. The DMA transfer may be controlled by the integrated circuit. The DMA transfer may be controlled by the second processor.

The method may include, at the integrated circuit: determining that one or more portions of the one or more frames has been received from the medical imaging device; and transmitting a signal to the second processor when a determination has been made that the one or more portions of the one or more frames has been received from the medical imaging device. The method may include, by the second processor: receiving the signal from the integrated circuit indicating that a complete frame of the one or more frames has been received from the medical imaging device; and causing the first processor to initiate processing the plurality of data portions upon receiving the signal from the integrated circuit indicating that a complete frame of the one or more frames has been received from the medical imaging device. The method may include, by the first processor: receiving the signal from the integrated circuit indicating that a complete frame of the one or more frames has been received from the medical imaging device; and initiating processing the plurality of data portions upon receiving the signal from the integrated circuit indicating that a complete frame of the one or more frames has been received from the medical imaging device.

The method may include, by the integrated circuit, performing one or more image processing algorithms on the received one or more frames of video data.

The method may include, by the integrated circuit, receiving one or more processed images from the first processor and performing one or more image processing algorithms on the received one or more processed images.

The method may include, by the integrated circuit, receiving one or more processed images from the first processor using a direct memory access (DMA) transfer. The method may include, by the integrated circuit, outputting the received one or more processed images to the electronic display using one or more output ports. The one or more output ports may include high-definition multimedia interface (HDMI) output ports. The one or more output ports may include DisplayPorts compatible output ports. The one or more output ports may include Serial Digital Interface (SDI) output ports.

The computing system may include a multiplexer comprising a first input communicatively coupled to the output port of the integrated circuit, a second input of the multiplexer communicatively coupled to an output port of the first processor, and an output port communicatively coupled to the electronic display, and the method may include, by the multiplexer, selecting the first input or the second input to be transmitted to the electronic display using the output port based on one or more control signals received from the integrated circuit.

The method may include, by the integrated circuit: receiving an image from the first processor to be overlaid on the one more received processed images from the first processor; superimposing the received image onto the one or more received processed images to generate a composite image; and transmitting the composite image to the electronic display.

The integrated circuit may be a field programmable gate array (FPGA).

The method may include, by the integrated circuit, controlling a light source.

The method may include, by the integrated circuit: determining if the first or second processor has failed; and in accordance with determining that the first or second processor has failed: performing one or more image processing algorithms on the received one or more frames of video data to generate one or more processed frames of video data and transmitting the one or more processed frames of video data to the electronic display.

The one or more frames of video data may be received in a mobile industry processor interface (MIPI) camera serial interface (format).

The method may include, by a third processor, performing one or more image signal processing algorithms on the received one or more frames of video data. The one or more image signal processing algorithms may include a de-mosaic algorithm. The one or more image signal processing algorithms may include a noise reduction algorithm.

Processing the plurality of data portions may include applying one or more image signal processing algorithms selected from the group consisting of: Pixel defect correction, color leakage correction, de-mosaic, spatial and temporal noise reduction filters, sharpening filters, color space conversion, image stabilization, overlay of multiple image sensors, image augmentation, gamma correction, dewarping, and distortion correction.

The method may include, by the second processor, executing an operating system configured to manage operation of the first processor.

The first processor may be a graphics processing unit (GPU).

The method may include, by the first processor, controlling a light source.

The method may include, by the second processor, controlling a light source.

Processing the plurality of data portions may include applying one or more artificial intelligence applications to the plurality of data portions. The first processor may include one or more tensor cores configured to perform matrix operations. The one or more tensor cores may be configured to apply the one or more artificial intelligence applications to the plurality of data portions.

The memory may be a buffer that is part of the first processor.

The memory may be a system memory shared by the first and second processors.

The method may include, by the first processor, performing one or more iterative algorithms on the plurality of data portions, wherein performing an iterative algorithm comprises: applying a first common instruction to each data portion of the plurality of data portions to generate a plurality of first processed data portions; storing each data portion of the plurality of first processed data portions in the memory; and applying a second common instruction to each data portion of the plurality of first processed data portions stored in the memory to generate a plurality of second processed data portions.

The method may include, by the first processor, performing video encoding on the received one or more frames of video data. Performing video encoding on the received one or more frames may include applying H.264 encoding on the received one or more frames of video data.

The method may include, by the first processor, performing one or more image processing algorithms on the one or more frames of video data selected from the group consisting of pixel defect correction, color leakage correction, demosaicing, spatial filtering, temporal noise filtering, sharpening filtering, color space conversion, image stabilization, image augmentation, gamma correction, dewarping, image compression, image decompression, and distortion correction.

The electronic display and the medical imaging device may be operated using a common clock signal generated by the computing system.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE FIGURES

The invention will now be described, by way of example only, with reference to the accompanying drawings, in which.

DETAILED DESCRIPTION

Figure 1:
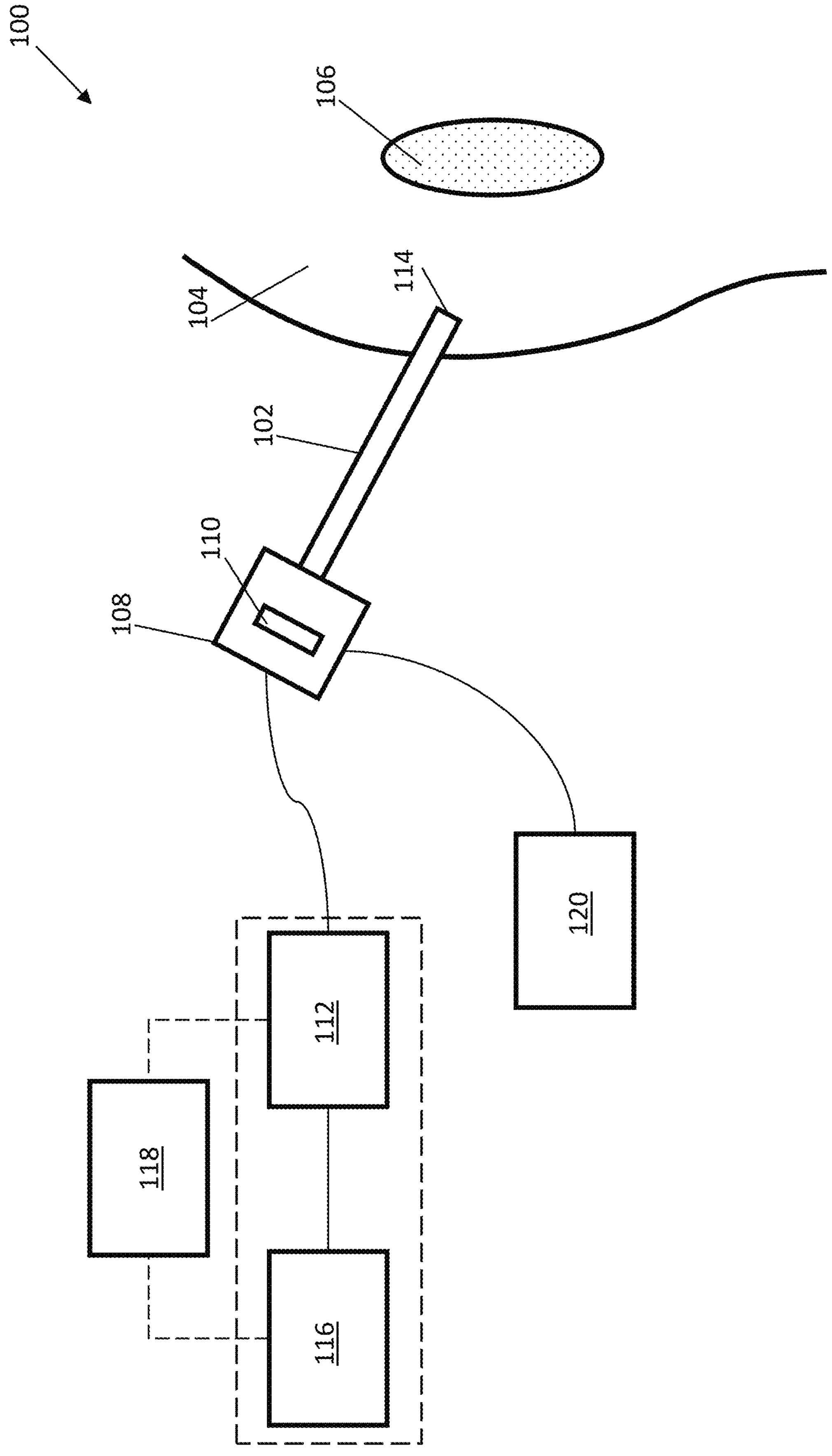
FIG. 1 illustrates an exemplary endoscopy system according to examples of the disclosure.

Reference will now be made in detail to implementations and example of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described herein are systems and methods for processing medical imaging data using one or more SIMD processors. In one or more examples, an endoscopic camera can be communicatively coupled to an embedded SIMD processing unit that includes a SIMD processor, a memory, and a general CPU. In one or more examples, image data collected from a medical imaging device can be stored in the memory and can be processed using the SIMD processor. In one or more examples, the SIMD processor can be controlled by the CPU, which can be programmed to operate the SIMD processor so as to apply one or more image processing algorithms on the image data stored in the memory of the embedded processing unit. In one or more example, the embedded processing unit can be connected to a display and can transmit processed imaging data to the display which can then be displayed during a surgical procedure. In one or more examples, the imaging data can be received by a FPGA that include a write DMA, which can be configured to collect frame data from the imaging device (such as a camera) and store it in a temporary memory. In one or more examples, once an entire frame has been collected by the write DMA of the FPGA, the data can then be transferred to the embedded processing unit for further processing.

In one or more examples, the embedded unit can be directly coupled to a display and thus can directly output any processed imaging data to the display. In one or more examples, the embedded processing unit can be connected to an FPGA which can include a read DMA, which can collect processed frame data from the embedded processing unit and then transfer the data to the display for rendering. In one or more examples, the embedded system can include the ability to either output its processed image data directly to a display or output its processed image data to the read DMA, which can then output the data to the display. In one or more examples, the SIMD processor can be part of a computing system (as opposed to an embedded unit).

In the following description of the various example, it is to be understood that the singular forms “a,” “an,” and “the” used in the following description are intended to include the plural forms as well, unless the context clearly indicates otherwise. It is also to be understood that the term “and/or” as used herein refers to and encompasses any and all possible combinations of one or more of the associated listed items. It is further to be understood that the terms “includes, “including,” “comprises,” and/or “comprising,” when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as “processing,” “computing,” “calculating,” “determining,” “displaying,” “generating” or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each connected to a computer system bus. Furthermore, the computing systems referred to in the specification may include a single processor or may be architectures employing multiple processor designs, such as for performing different functions or for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present disclosure as described herein.

FIG. 1 illustrates an exemplary endoscopy system according to examples of the disclosure. System 100 includes an endoscope 102 for insertion into a surgical cavity 104 for imaging tissue 106 within the surgical cavity 104 during a medical procedure. The endoscope 102 may extend from an endoscopic camera head 108 that includes one or more imaging sensors 110. Light reflected and/or emitted (such as fluorescence light emitted by fluorescing targets that are excited by fluorescence excitation illumination light) from the tissue 106 is received by the distal end 114 of the endoscope 102. Light from a light source 120 is propagated by the endoscope 102, such as via one or more optical components (for example, one or more lenses, prisms, light pipes, or other optical components), to the camera head 108, where it is directed onto the one or more imaging sensors 110. One or more filters (not shown) may be included in the endoscope 102 and/or camera head 108 for filtering a portion of the light received from the tissue 106 (such as fluorescence excitation light).

The one or more imaging sensors 110 generate pixel data that can be transmitted to a camera control unit 112 that is communicatively connected to the camera head 108. The camera control unit 112 generates a video feed from the pixel data that shows the tissue being viewed by the camera at any given moment in time. The video feed can be transmitted to an image processing unit 116 for further image processing, storage, display, and/or routing to an external device (not shown). The camera control unit 112 and the image processing unit 116 may comprise parts of a single combined unit as indicated in FIG. 1 by the dashed box. The images can be transmitted to one or more displays 118, from the camera control unit 112 and/or the image processing unit 116, for visualization by medical personnel, such as by a surgeon for visualizing the surgical field 104 during a surgical procedure on a patient. It will be appreciated that the endoscope 102 can be inserted into the surgical cavity 104 prior to the start of a method for processing and displaying medical imaging data onto the one or more displays 118.

In this example, image processing unit 116 can apply one or more image processing algorithms to any data received from the camera control unit in order to improve the image quality of the data before it its transmitted to the one or more displays 118. The image processing unit 116 may comprise a combination of ASICS, FPGAs, digital signal processors (DSP) and generalized CPUs that can be collectively coupled to one another so as to carry out any image processing tasks on the image data received from camera control unit 112. However, such processing units, while capable of performing a myriad of image processing tasks, may not be able to perform more complex image processing tasks without introducing unacceptable latency between the moment when an image is captured by the camera, and the moment that that image is displayed. The reason why the conventional image processing architectures described above may not be able to implement more complex processing algorithms without introducing significant display lag into the system, lies in the data/instruction processing architecture of the components found in the image processing unit. For instance, and as described below, many processing components found in image processing use multiple instruction multiple data (MIMD) processing techniques to affect any algorithms or processing that are performed on acquired medical imaging data. CPUs, DSPs, and ISPs, in particular, which are generally used by image processing units to perform the image processing algorithms, use MIMD processing techniques. But as described below, this processing technique may not lend itself to more complex image processing algorithms without introducing significant delay to the processing time required to implement such algorithms.

Figure 2A:
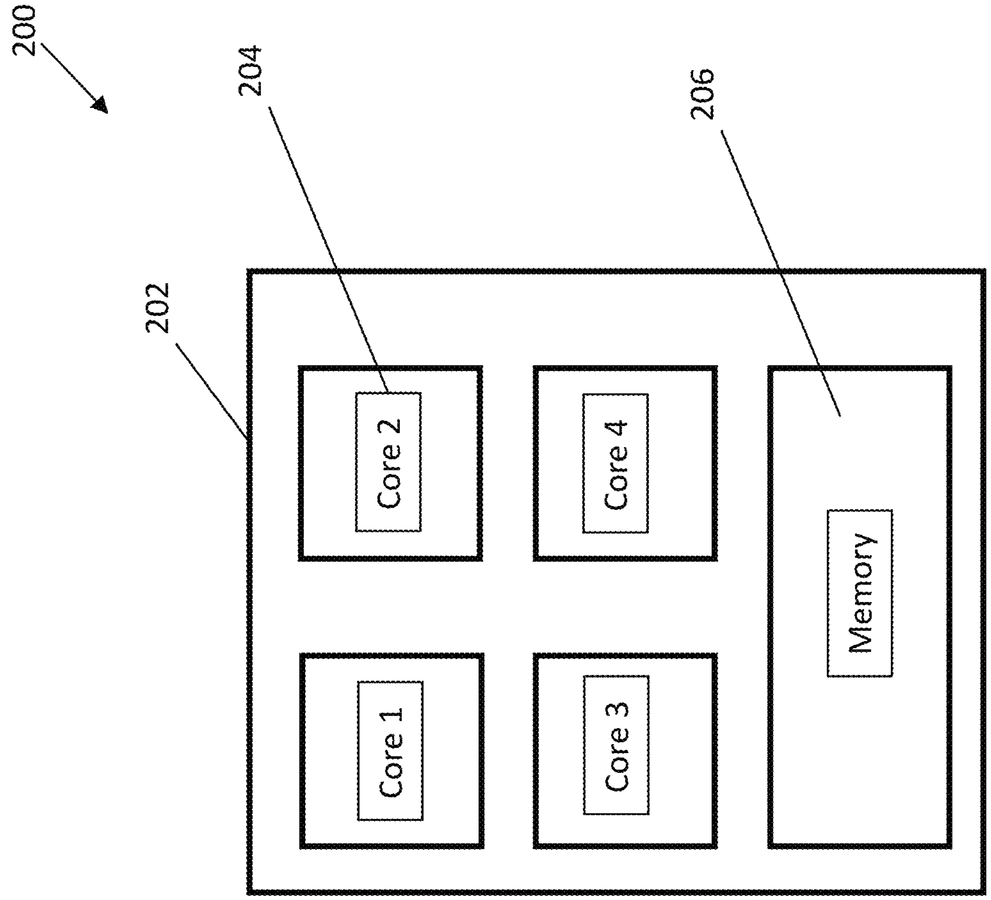
FIGS. 2A-2B illustrate exemplary processing architectures according to examples of the disclosure.

FIG. 2A illustrates an exemplary MIMD processing architecture according to examples of the disclosure. The architecture 200 of FIG. 2 can represent an exemplary architecture of a CPU, DSP, and/or ISP that individually or collectively can be used to process medical imaging data. The processor 202 can include one or more components (described in detail below) that can collectively implement a series of processing tasks based on instructions provided to it. The architecture 200 of the processor 202 of FIG. 2 can include a plurality of processing cores 204. Each processing core 204 can be responsible for performing a single task at any given moment in time. Each core 204 can include components such as an arithmetic logic unit (ALU), a cache memory, and a control unit that can coordinate the functions of the core. In one or more examples, a core 204 can process a series of tasks serially, by taking in one or two data objects from a memory and performing a task (such as adding, subtracting, etc.) on the data, and then storing a result of the task). Each core operates instructions serially, while the multiple cores 204 in a single process 202 allow for the processor 200 to perform multiple instructions (i.e., tasks) in parallel with one another, thus increasing the overall processing speed of the processor 200. Thus, the processor 200 processes multiple instructions simultaneously on multiple data objects, therefore making it a MIMD processing architecture.

The processing architecture described above with respect to FIG. 2A can be configured to handle a wide-range of tasks quickly but may be limited as to the number of tasks it can perform concurrently. Each core can perform a single task at a time, and thus the amount of tasks that can be performed concurrently is limited to the number of cores contained within a processor. Each processor core includes its own task scheduler (not pictured) that manages the instructions being executed by the core at any given moment. Thus, since each core has its own task scheduler, each core can execute a task concurrently with the tasks being performed on other cores of the same processor. Each core of the processor can be configured to perform its tasks quickly and efficiently, albeit serially.

For some computing applications, however, the serial nature of a CPU or processor with an architecture described above with respect to FIG. 2A may lead to inefficiencies and slow operation. For instance, in image processing contexts, algorithms that perform complex algorithms on a digital image frame may need to be processed concurrently so that they can be rendered to a display with minimal latency. Using an architecture such as the one discussed above with respect to FIG. 2A, in order to perform a complex algorithm on an entire digital image frame, each pixel would have to be operated on in a serial manner (or a few pixels concurrently depending on the number of cores in the processor). Operating on a digital image frame on a pixel-by-pixel basis, rather than performing the algorithm on the entire frame concurrently, can lead to unacceptable processing times, which can mean that the image processing algorithm can delay the time between when an image was captured to the time when the image is displayed, meaning that the image is not a "real-time" image. In the context of medical imaging such a delay may be unacceptable and lead to unsafe operating conditions or surgical error.

Since many image processing algorithms perform the same task on an entire frame of data, a processing architecture in which a single task can be performed simultaneously on multiple data objects (i.e., pixels) simultaneously could allow for the implementation of more complex image processing algorithms without significant latency. A serial architecture, such as the one described above, cannot execute a single instruction on many data objects simultaneously because the architecture of such processors operate in a serial manner. A processing architecture that can perform massive parallel processing (MPP) using a single instruction may lend itself better to implementing image processing algorithms.

Figure 2B:
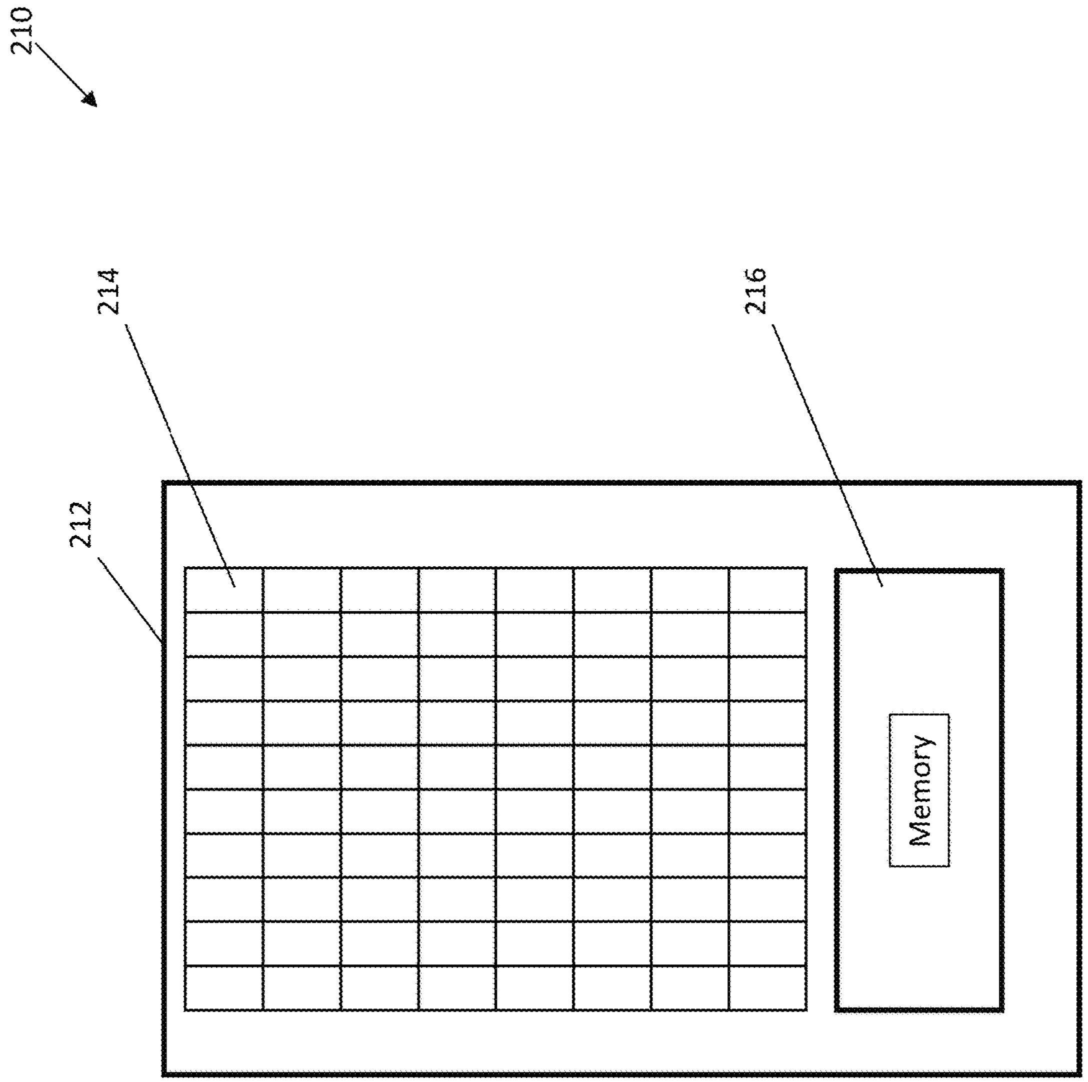

FIG. 2B illustrates an exemplary SIMD processing architecture according to examples of the disclosure. The architecture 210 of FIG. 2B includes a processor 212 which includes a large number of processing cores 214. The processing cores 214 of processor 212 may only include a subset of the capabilities of core 204 of the architecture 200 of FIG. 2A, thus allowing them to be smaller, which can mean that the processor 212 can fit many more cores on the chip than the processor 202 of FIG. 2A. In other words, a core 214 of processor 212 may have a limited instruction set. Furthermore, the core 214 may not process a single instruction as quickly as its counterpart from FIG. 2A. Thus, the core 214 is less capable in general than a core from a CPU processor, but it is smaller thus allowing more of them to be included in a single processor. For example, a conventional CPU may include 4 cores, but in contrast a SIMD architecture like the one of FIG. 2B can allow for 40,000 separate cores.

In one or more examples, all of the cores 214 of processor 212 can be instructed by a single task scheduler (not pictured), which means that all of the cores can perform the same task (i.e., a single instruction) on a massively parallel basis. Each core 214 can receive one or more data objects stored in a memory 216, and each perform the same instruction/task on their received data objects in parallel to one another. A processor with a SIMD architecture can thus perform image processing tasks on a frame-by-frame basis meaning that it can perform often complex imaging tasks with minimal latency as compared to a conventional CPU or DSP. However, an image processing system, such as the image processing unit 116 of FIG. 1, may require more than just a SIMD processor to implement all the required functionality. For instance, the image processing unit may need to perform other tasks other than image processing such as receiving imaging data, storing imaging data, interfacing with a computer display, running an operating system, etc., that may not be feasibly implemented using a SIMD processor. Thus, in one or more examples, and as described in detail below, a SIMD processor can be utilized as a part of a system that includes one or more other processing components that collectively receive imaging data, store imaging data, process imaging data, and transmit imaging data to a display. As described in further detail below, the components of such a system can be configured vis-à-vis one another so as to minimize the amount of data latency in the system while utilizing SIMD processing capabilities to perform complex image processing algorithms.

Figure 3:
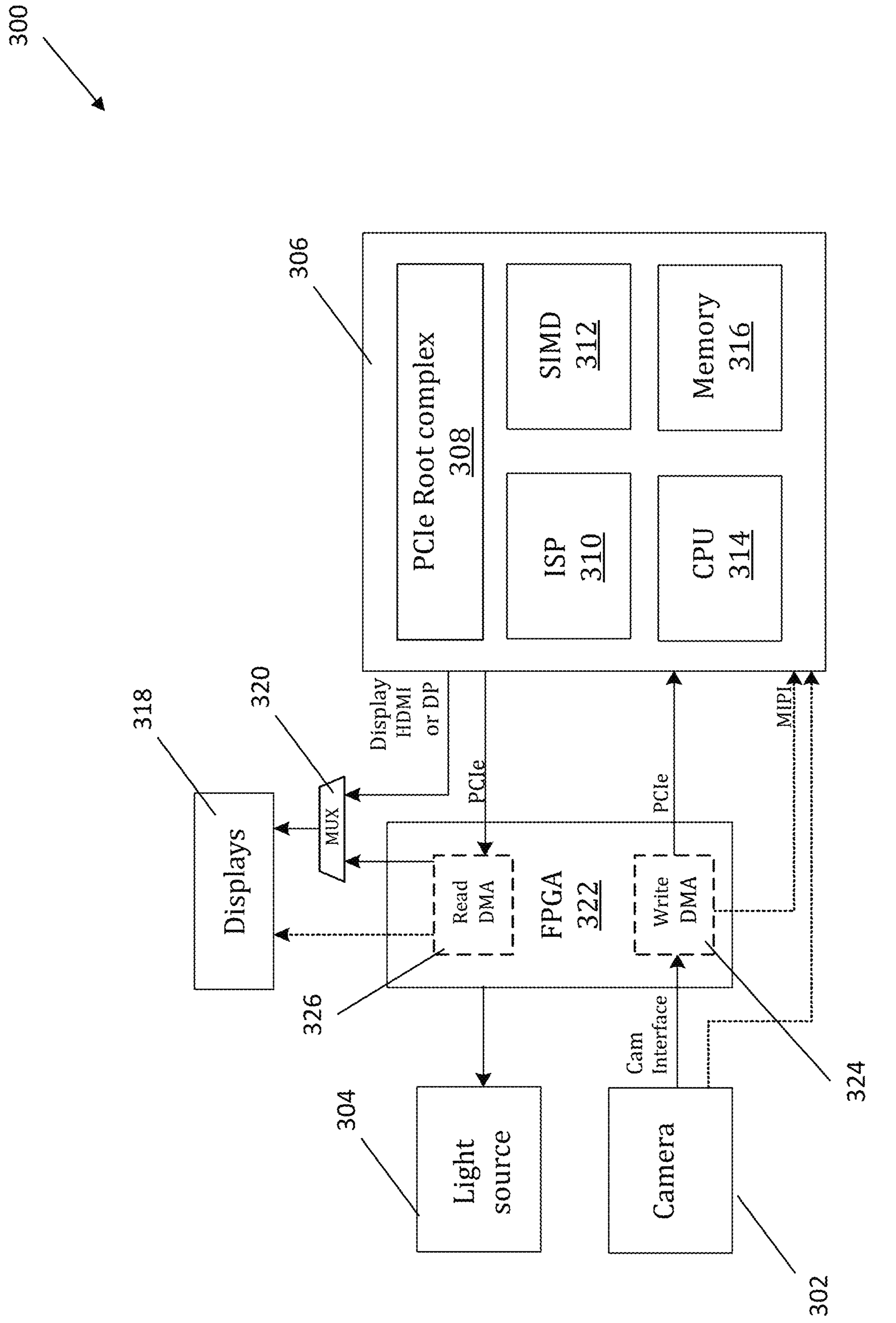
FIG. 3 illustrates an exemplary medical image processing system with SIMD processing capabilities according to examples of the disclosure.

FIG. 3 illustrates an exemplary medical image processing system with SIMD processing capabilities according to examples of the disclosure. The medical image processing system 300 can perform the functions associated with camera control unit 112 and image processing unit 116 discussed above with respect to FIG. 1. System 300 can include a camera 302 that includes one or more image sensors that are configured to capture image data of a tissue area of a patient, convert the image data to a digital representation, and transmit the digital data to one or more components of the system 300 (as described in further detail below).

In one or more examples, the camera 302 can transmit its acquired medical imaging data to FPGA 322. The camera 302 can be connected to FPGA 322 using a custom interface protocol, or alternatively using any commercially available interface such as the Mobile Industry Processor Interface Camera Serial Interface 2 (MIPI CSI-2), Ethernet, coaxial cable, or any other standard suitable for transferring data acquired by the camera 302 to the FPGA 322. FPGA 322 can perform multiple functions associated with the image processing unit 300. For instance, the FPGA 322 can convert the received data to another format that may be more suitable for processing such as Peripheral Component Interconnected (PCI) Express. The FPGA can also be configured to perform other image pre-processing tasks that may be better suited to be performed using non-SIMD architecture. In order to minimize latency, the FPGA may not include a frame buffer (i.e., a temporary memory large enough to store an entire frame), but may only buffer the amount of pixel data that is necessary to form the PCI express packets and mitigate any back pressure from a PCI express bus that is connected to other components of the system 300.

In one or more examples, the transfer of imaging data from camera 302 to FPGA 322 can be conducted using a Direct Memory Access (DMA) transfer that can be controlled by the FPGA 322. The camera 302 can be connected to FPGA 322 via a Write DMA 324. Write DMA 324 can be configured to allow camera 302 to access the main memory of the processor 306 (described in further detail below) independently of any central processing unit or component. Thus, for example, FPGA 322 can initiate a transfer of data from the camera 302 to the write DMA 324 and perform other tasks while the image data is being transferred to write DMA 324. Once the write DMA 324 has completed transferring a frame of image data from the camera, the DMA 324 can send an interrupt to the FPGA using a DMA controller letting it know that a frame of data has been transferred. FPGA 322 can then signal the processor 306 (described in further detail below) when a full frame is received, and the processor 306 can then coordinate the transfer of the data to its own internal memory. The write DMA can send an interrupt to the FPGA when only a portion of a frame (i.e., a sub-frame) has been transferred. The FPGA can packetize the received image sensor data once it is received, and transmit it to a PCIe address to memory that can be accessed by a SIMD process 312 of the processor 306. The processor 306 can control the write DMA 324 instead of the FPGA 322. Write DMA 324 can transfer the data to processor 306 using a PCIe format or alternatively can use a MIPI format. Camera 302 can transmit the acquired image data directly to processor 306 without first transferring the data to the FPGA 322. In one or more examples, the camera 302 formats the data into a format such as MIPI and transfers the data directly to the memory of processor 306.

In addition to "writing" image data to processor 306, FPGA 322 can also "read" data from the processor 306. The output images from processor 306 can be transferred back to FPGA 322 using read DMA 326. Read DMA 326 can be configured similarly to write DMA 324 and can be configured to read data from the processor 306 once the processor 306 signals that a full frame of data is ready to be transferred to the FPGA 322. Read DMA 324 can store data received from processor 306 and can output the data to display 318 for rendering on an electronic display which can be viewed by a surgeon or other medical personnel during a surgical or other medical procedure.

Read DMA 324 can be configured to transfer output images to a display 318 for rendering. FPGA 322 can convert the images received via read DMA 324 and convert the stored images to a format compatible with display 318 such as HDMI, DisplayPort, SDI, DVI, or similar standard. FPGA 322 can provide further image processing to the images it receives from processor 306 before transmitting it to display 318. Such an arrangement can allow for detailed control of the display output while still leveraging the composition capabilities of the processor 306. FPGA 322 can include a minimalistic image processing engine that can be activated if the processor 306 fails in any way. This is useful for systems where the lack of video creates a risk or is otherwise not acceptable and the risk for failure of the more complex processor 306 is too large. The minimalistic image processing generates an image good enough to view and complete the surgery. In one embodiment the FPGA expects a watchdog signal from the processor 306 in a defined interval and if the signal is missed, the backup image processing block in the FPGA is activated. In one or more examples, one or more components of the system 300 including FPGA and/or processor 306 can generate a clock signal that can be used to simultaneously control display 318 and camera 302, so as to coordinate the timing of transmission and display of data, thereby further reducing the overall latency of the system by avoiding situations in which the data stored in the FPGA 322 has to wait for the data stored in the processor 306 to be output to display 318 which would add more latency to the overall image processing pipeline. In order to keep the latency low, it may be necessary to lock the vertical sync (vsync) of the display 318 with the vsync of the image sensor(s) of camera 302. If this relationship can be locked, the latency can be lowered by up to 1 frame (0.5 frames on average). In order to lock the vsync, it may be necessary that the camera and display are running with the same clock and thus their v-sync has a constant fixed relationship. The clock and vsync of the display output of a SIMD processor 312 can be generated by the SIMD processor and cannot be influenced by other hardware. Thus, the clock and vsync of the SIMD processor 312 may be detected and the camera 302 can be driven according to this clock. In one or more examples, SIMD processor 312 can be configured to lock to an external sync signal. In this case, the vsync from the camera 302 could also drive the vsync of the SIMD processor 312.

FPGA 322 can receive the display output from processor 306 (e.g., HDMI or DP signal) either as pass-through (the FPGA 322 then forwards it to the display), as a split signal (the FPGA 322 gets a clone of the signal that drives the display), or as a separate display output. FPGA 322 can decode the signal and detect the pixel clock, screen resolution (if not known) and vertical sync. The camera 302 can run in slave mode. The FPGA 322 can use the determined pixel clock to generate the clock for the camera 302. Additionally, the FPGA 322 can use the detected vertical sync to generate a vertical sync to the camera 302. The vertical sync to the camera 302 can be at the same time as the one to the display 318, or any configured offset from it. This offset can allow for compensation for any latency in the system, thus the offset can be software controlled and configured so that the processing is finished just before the vertical sync of the display 318 is sent. The camera 302 can operate in master mode. In this case the camera clock can still be generated based on the display clock, and the software starts the camera 302 at the right moment to accomplish the required vsync offset.

In one or more examples, the processor 306 can transmit its output directly to the display 318. The output images are converted by processor 306 to a format compatible with the display 318 using one or more display ports associated with the processor such as HDMI, DisplayPort, SDI, DVI or similar. Alternatively, the output of processor 306 can be routed through a multiplexer 320 to the display 318. Multiplexer 320 can be controlled by FPGA 322 and can be used to either show the output from the processor 306 or FPGA 322 on the display 318. The processor 306 can include a PCI Express root complex unit 308 that can be used to packetize output data for transport on a PCI express bus to the display. Display 318 can include a touch screen to receive user inputs. In order to keep the latency low, it is necessary to lock the vertical sync (vsync) of the display with the vsync of the image sensor(s). If this relationship can be locked, the latency can be lowered by up to 1 frame (0.5 frames in average). In order to lock the vsync, it is necessary that the camera and display are running with the same clock and thus their vsync has a constant fixed relationship. Normally the clock and vsync of the display output of a GPU are generated by the GPU and cannot be influenced by hardware. Thus, in the preferred embodiment, the clock and vsync of the GPU is detected and the camera is driven according to this clock. Some GPUs do allow to lock to an external sync signal (e.g., high-performance Quadro using Sync II). In this case, the vsync from the camera could also drive the vsync of the GPU.

FPGA 322 can also be used to control a light source 304 (e.g., light source 120 of FIG. 1). Light source 304 can consist of one or more light emitting diodes (LEDs) or lasers and illuminates the area of the patient being viewed by the camera 302, either with white light, near-infrared light, or any other light as needed by the imaging system. The light source 304 can be connected using a light guide to the endoscope. The light source 304 can be controlled (e.g., adjusted intensity, pulsing, changing color) by FPGA 322. Additionally or alternatively, the light source 304 can be controlled by a microcontroller in or close to FPGA 322, and/or can be controlled by processor 306 and specifically the CPU 314 that is a part of the processor 306. In one or more examples, FPGA 322 or processor 306 can control the light source 304 such that the light is closely coupled/synchronized with the image acquisition.

In one or more examples, system 300 can include a processor 306 that serves as the main image processing engine of the system. The processor 306 of system 300 can include one or more components that collectively perform the image processing tasks associated with image processing unit 116 of system 100 of FIG. 1. Processor 306 can include a memory 316 that can store the image data transferred from camera 302 either through the FPGA 322 or directly from the camera itself as discussed above. Memory 316 can act as a shared memory between the various components of the processor 302 including processing cores associated with each component (described in further detail below).

In one or more examples, embedded processor 306 can include an image signal processor (ISP) 310. ISP 310 can be implemented as a special purpose processor that is specifically made and configured to perform specific algorithms. ISP 310 can be configured to perform certain standard (non-medical related) image processing algorithms such as image demosaicing, image compression/decompression, or image noise reduction. ISP 310 can employ a processor architecture such as the one discussed above with respect to FIG. 2A meaning that it performs its tasks in a serial manner with a small amount of concurrent processing capability. The ISP 310 can be used to conduct certain image processing tasks that are more efficiently and quickly handled by a processor that has a serial architecture such as the one described above with respect to FIG. 2A.

The processor 306 can include a SIMD processor 312. SIMD processor 312 can utilize a processing architecture similar to the one described above with respect to FIG. 2B, wherein the processor 312 includes a large number of cores that each operate on separate data objects in parallel using a single common instruction. The SIMD processor 312 can be suited for certain imaging algorithms in which a large number of pixels up to and including an entire frame are processed simultaneously. Examples of image processing algorithms in which entire frames (or large portions of image frames) are processed using a single instruction at a time include: pixel defect correction, color leakage correction, demosaicing, implementing spatial and temporal noise reduction filters, implementing sharpening filters, color space conversion, image stabilization, overlay of multiple image sensors (fluorescence), image augmentation, gamma correction, dewarping, image compression and decompression, and distortion correction. The above listed processing algorithms are meant as examples of the type of imaging algorithms that can be performed by the SIMD processor 312 and should not be seen as limiting to the disclosure. Indeed SIMD processor 312 can be utilized for any imaging algorithm that is better suited for the architecture of SIMD processor 312. The SIMD processor 312 can be configured to perform image compression algorithms such as H.264 and H.265. The SIMD processor 312 can be used to analyze the video and decide on the compression level required for the frame. Allowing the SIMD processor 312 to determine the level of compressing can allow for variable bit rate encoders that result in a low latency high quality video stream.

In one or more examples, the SIMD processor 312 can include a plurality of "tensor" processing cores. Tensor cores are processing cores that are specifically configured to accelerate matrix operations such as matrix multiplication. Tensor cores can be used by a SIMD to perform image processing algorithms that involve machine learning/AI operations. SIMD processor 312 can include only tensor cores, a mixture of tensor cores and generic processing cores, or only generic processing cores. Tensor cores can be used for generic matrix operations that are part of other image processing algorithms such as convolution filters or warping/rotational image processing operations. A SIMD process 312 can be implemented as a graphics processing unit (GPU) especially configured to operate with the other components contained in process 306.

In one or more examples, the SIMD processor 312 can transfer raw input images, intermediate processed images and/or fully processed images to a separate engine (local or in the cloud) for AI based image processing or analysis. This transfer can either be done with raw image data or with the compression processes described throughout the disclosure. The image data can be downscaled by one or more of the components of the system such as the processor 306 or the FPGA 322.

One or more intermediate steps of an image processing algorithm can be performed on a full frame and the result can be used to run another algorithm on the same set of pixels, which may allow for modification of all of the pixels of the frame based on the data of all the pixels of the frame. In at least some instances, this may result in, for example, the bottom right pixel of an input frame influencing the top left pixel on the output frame.

An SIMD processor 312 can perform iterative algorithms in which a set of instructions (one or more instructions) is performed on the full input frame of the image data, and the same or a different set of instructions is performed on one or more frames in an intermediate state of processing using results of the set of instructions performed on the full input frame. The intermediate frames of an algorithm can be stored in a memory (such as memory 316) and then used by the SIMD processor for further processing. An iterative algorithm may use a portion of the input frame, such as a region of interest. An iterative algorithm may include at least one intermediate state, at least two intermediate states, at least three intermediate states, at least four intermediate states, at least five intermediate states, etc., with all steps of the iterative algorithm being calculated within the period of one frame. An exemplary iterative algorithm can improve auto-gain/exposure control by adjusting the currently processed frame with digital gain to achieve a faster (e.g., zero latency) auto-gain loop.

The above listed image processing algorithms can be performed on a frame-by-frame basis using the SIMD processor 312. In other words, each of the pixels that make up a single frame of data can be loaded into its own processing core within SIMD processor 312, and processed simultaneously using a single common instruction. The processing can be done on a sub-frame basis. In the case of processing on a sub-frame basis, the processing performed by SIMD processor 312 can begin as soon as part of the frame (instead of the full frame) is transferred to the SIMD processor 312. Image processing algorithms that may not require having the full frame to be accessible, can operate on a sub-frame basis as described above. Algorithms that may need neighboring pixels of the sub-frame, can be performed by using an overlapping apron between sub-frame segments. Some algorithms can be processed at a sub-frame level while other algorithms can be executed once the full frame is received. Algorithms requiring a full frame of imaging data can use the received full-frame and/or the results from the algorithms performed at the sub-frame level as input. In one or more examples, and in the case of sub-frame processing, the results from the sub-frame level algorithms can be combined into a full frame at some point in time before the frame is sent to the display for rendering on a screen. Processing image data using SIMD processor 312 on a sub-frame basis can lead to lowering the processing latency of the entire imaging system 300 up to almost one frame.

The processor 306 can include a central processing unit (CPU) 314. CPU 314 can be used to control SIMD processor 312 as well as ISP 310, and can work to coordinate the operation of the components within the system 300 so as to perform the desired image processing tasks. CPU 314 can execute an operating system (such as Linux or Windows). CPU 314 can also coordinate the transfer of imaging data from the camera 302 to the processor 306, and can also optionally transfer any processed images (or any intermediate state) to memory 316 for further processing. CPU 316 can transfer processed image data to a persistent storage, such as a hard drive, flash drive or SSD. CPU 314 can perform some steps of the image processing not already performed by SIMD processor 312 or ISP 310. CPU 314 can be attached to a network, and can coordinate the streaming of medical imaging data to additional locations outside of the operating theater.

As discussed above, in one or more examples, image data from camera 302 can be transferred to the processor 306 via DMA transfer in the FPGA 322, and specifically by write DMA 324. The transfer of imaging data between the FPGA 322 and the processor 306 can be achieved in multiple ways. For instance, the write DMA 324 of FPGA 322 can transfer the image sensor data over a PCI express bus to the system memory 316 of processor 306. SIMD processor 312 can then initiate a second DMA transfer from the system memory 315 to an internal memory (not pictured) of the SIMD processor 312 for processing. Additionally or alternatively, the write DMA 324 of FPGA 322 can transfer the image sensor data to the processor 306 by directly transferring the image sensor data to the internal memory of SIMD processor 312 without having to first store the data in system memory 316. Additionally or alternatively, the system memory 316 can be shared with the SIMD processor 312 or SIMD processor 312 can access the system memory 316 directly without requiring the data to be first stored in a memory that is internal to the SIMD processor.

Figure 4:
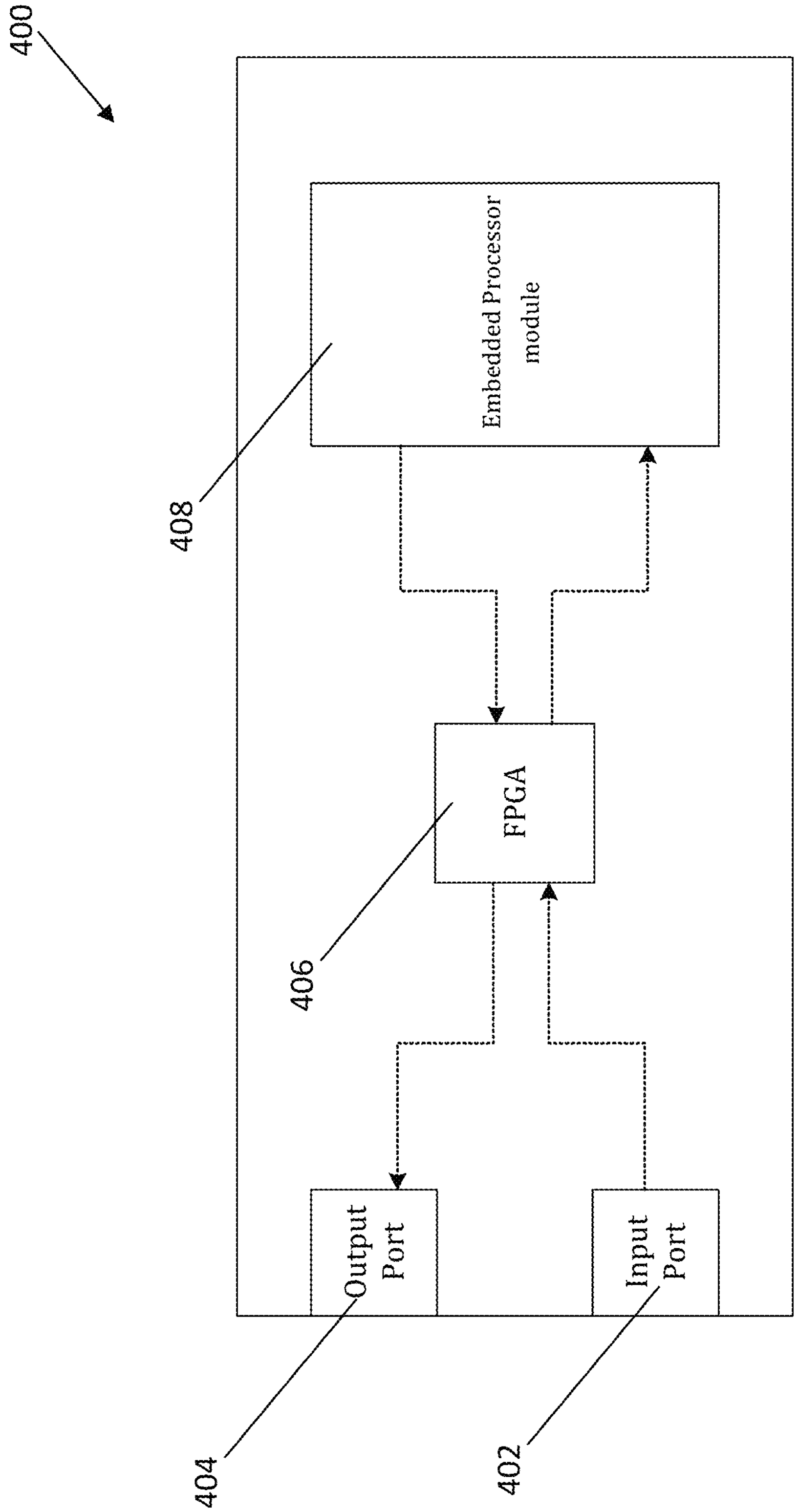
FIG. 4 illustrates an exemplary architecture for a medical image processing system according to examples of the disclosure.

The example system 300 of FIG. 3 utilizes an FPGA to transfer data from the camera to the SIMD processor, and also utilizes the same FPGA to transfer data from the SIMD processor to the display as described above. Thus, the FPGA stands between the input and output ports of the image processing unit (such as system 300) and the main processing unit that includes the SIMD processor (in addition to other components as described in detail above). FIG. 4 illustrates an exemplary architecture for a medical image processing system according to examples of the disclosure. The system architecture 400 of FIG. 4 can represent a simplified block diagram of the system 300 of FIG. 3 so as to better illustrate the main components of system 300 and their connections to one another.

The system architecture 400 of FIG. 4 can illustrate the layout of a chip board populated with the relevant components needed to implement the system. Architecture 400 can include input port 402 that is configured to receive image data from an image sensor (as described in detail above.) Input port 402 can be communicatively coupled to FPGA 406 so that data received at the input port 402 can be routed to FPGA 406, which using the systems and methods described above, can store the data received on the input port 402 and eventually transfer the data to embedded processor module 408 (which is substantially similar to processor 306 of system 300).

Embedded processor module 408 can process the received image data and then output the processed data back to FPGA 406 (using the systems and methods described above). FPGA 406 can be communicatively coupled to an output port 404. FPGA 406 can transmit any data received from embedded processor module 406 to output port 404 which can be connected to a display or other component (such as a multiplexer as described above) and ultimately rendered on a display.

The image processing system may not require an FPGA to intervene between the embedded processor module and both of the input and output ports of the device. The embedded processor module can interface directly with its own input or output ports to directly receive data from a camera or transmit data to a display without requiring the intervention of an FPGA. While eliminating the FPGA or minimizing its role in the processing of data can lead to overall reduced system latency, it can also add complexity to the design and requirements of the embedded processor module.

Figure 5:
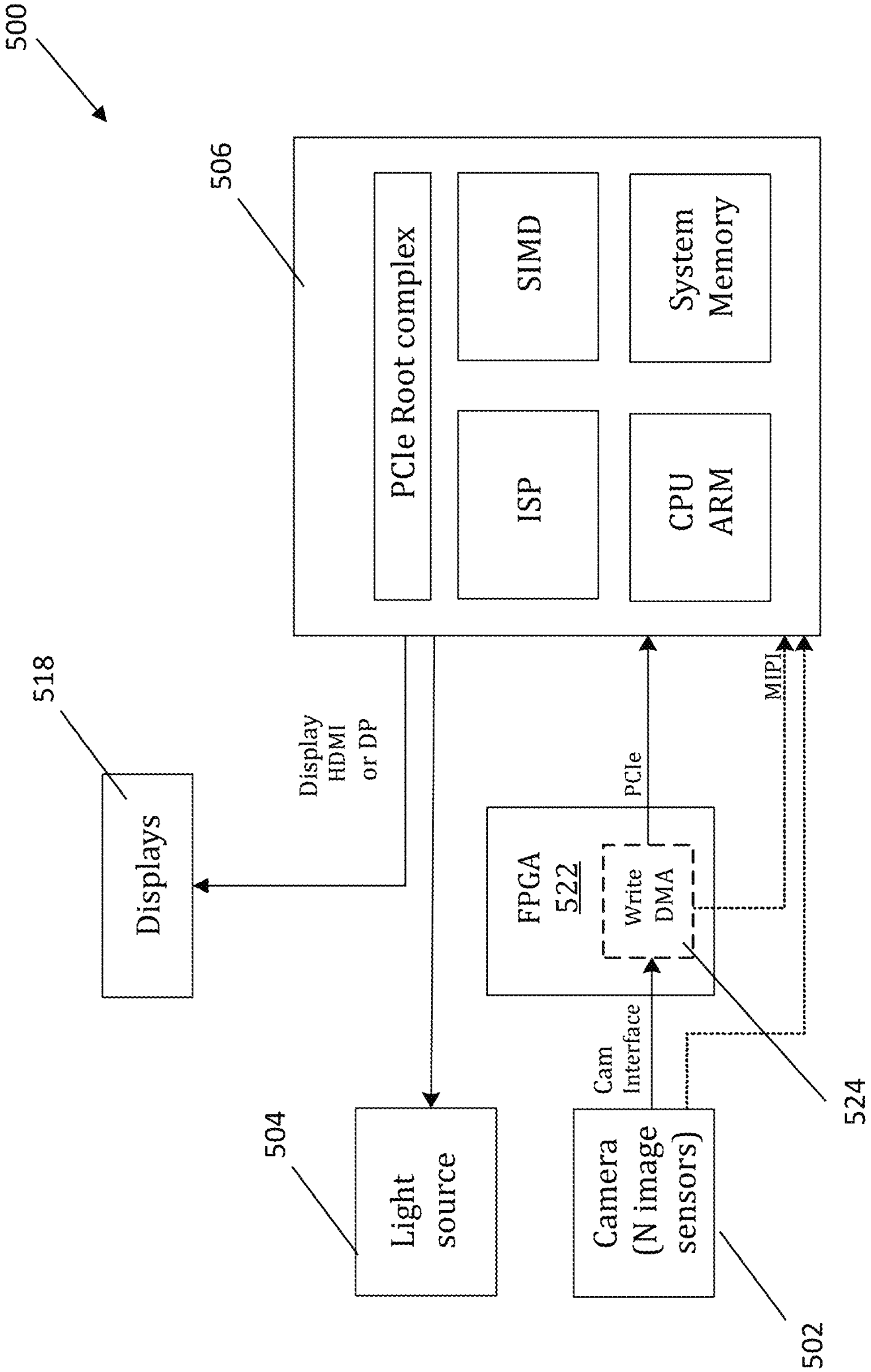
FIG. 5 illustrates another exemplary medical image processing system with SIMD processing capabilities according to examples of the disclosure.

FIG. 5 illustrates another exemplary medical image processing system with SIMD processing capabilities according to examples of the disclosure. The example system 500 of FIG. 5 can be substantially similar to the example system 300 of FIG. 3. Thus, a discussion of the functionality of camera sensor 502, light source 405, processor 506, and display 518 can be found above with respective to their respective counterpart components of system 300. In one or more examples, FPGA 522 can have similar functionality to its system 300 counterpart. However, rather than include both a read DMA and a write DMA, FPGA 522 can include only a write DMA 524 that operates in substantially the same manner as write DMA 324 of system 300. Thus, for a detailed discussion of the operation of write DMA 524, the discussion of write DMA 324 can be referenced above.

The example system 500 includes an embedded processor 506 which includes the same components and functionality as processor 306 described above with respect to FIG. 3. However, in one or more examples, processor 506 can transmit processed image data directly to display 518 rather than transmitting the data to an FPGA. In one or more examples, the output images are converted by processor 506 to a format compatible with the display 518 using one or more display ports (not pictured) associated with the processor such as HDMI, DisplayPort, SDI, DVI or similar. Processor 506 can transmit the image data directly to the display 518 via OpenGL or similar interface. The processor 506 can be configured to also modify the output images with on-screen displays (OSD) or augmented reality overlays prior to transmitting the image to the display.

Figure 6:
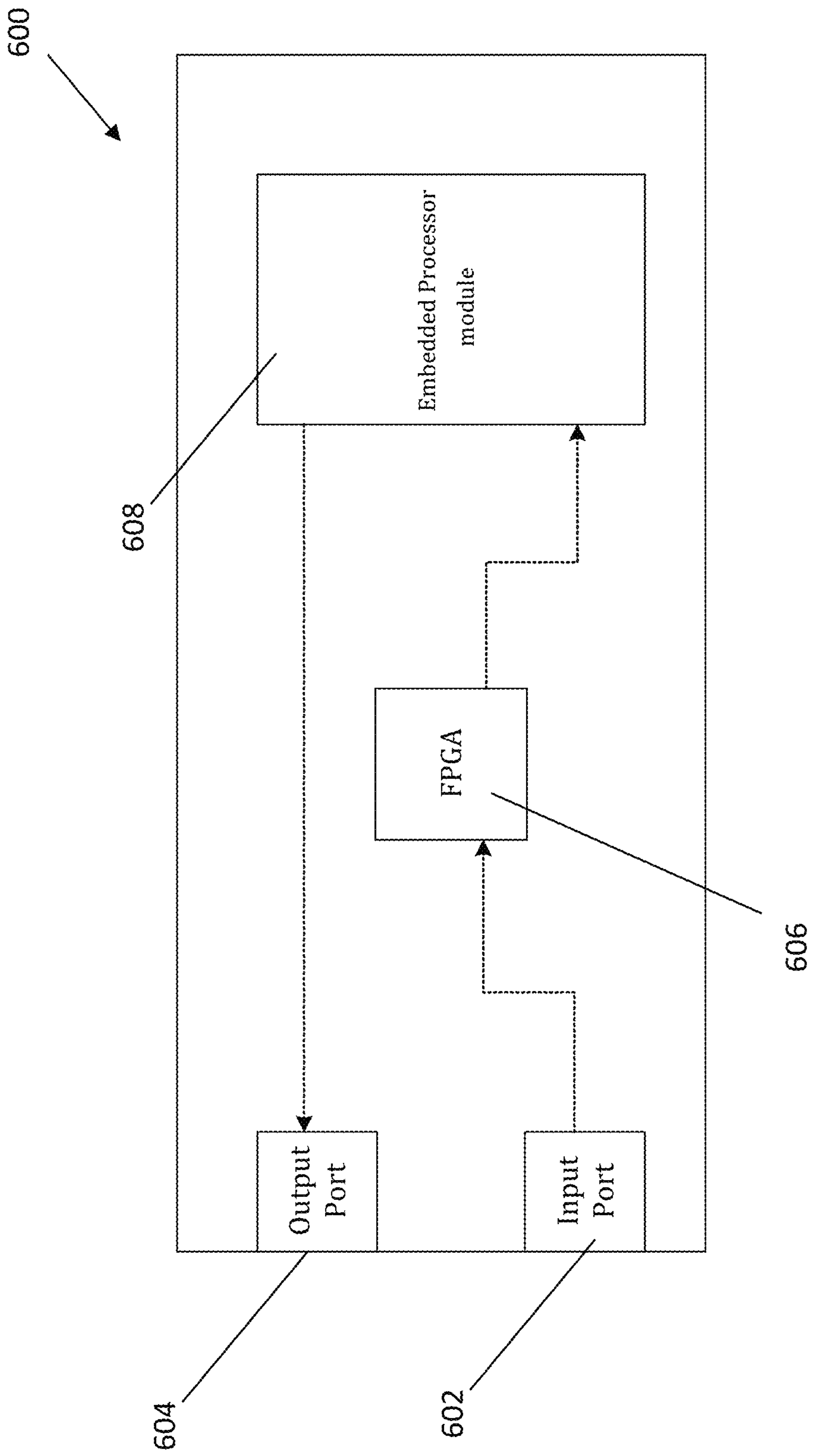
FIG. 6 illustrates another exemplary architecture for a medical image processing system according to examples of the disclosure.

The example system 500 described above includes an FPGA that is used to interface the received camera data to the processor 506. Thus, in the example of FIG. 5, the FPGA stands in between the input of the imaging unit and the embedded processor so as to collect data and pass it to the embedded processor once a full frame data (or sub-frame) has been received. FIG. 6 illustrates another exemplary architecture for a medical image processing system according to examples of the disclosure. The system architecture 600 of FIG. 6 can represent a simplified block diagram of the system 500 of FIG. 5 so as to better illustrate the main components of system 500 and their connections to one another.

The system architecture 600 of FIG. 6 can illustrate the layout of a chip board populated with the relevant components needed to implement the system. In one or more examples, architecture 600 can include input port 602 that is configured to receive image data from an image sensor (as described in detail above.) Input port 602 can be communicatively coupled to FPGA 606 so that data received at the input port 602 can be routed to FPGA 606, which using the systems and methods described above, can store the data received on the input port 602 and eventually transfer the data to embedded processor module 608 (which is substantially similar to processor 506 of system 300).

Embedded processor module 608 can process the received and then output the processed data directly to output port 604. As described above with respect to FIG. 6, the embedded processor module 608 (which represents processor 506 of FIG. 5) can convert any output images to a format compatible with a display connected to output port 604 using one or more display ports (not pictured) such as HDMI, DisplayPort, SDI, DVI or similar. Embedded processor module 608 can transmit the image data directly to the output port 604 using OpenGL or similar interface. The processor 608 can be configured to also modify the output images with on-screen displays (OSD) or augmented reality overlays prior to transmitting the image to the display.

Figure 7:
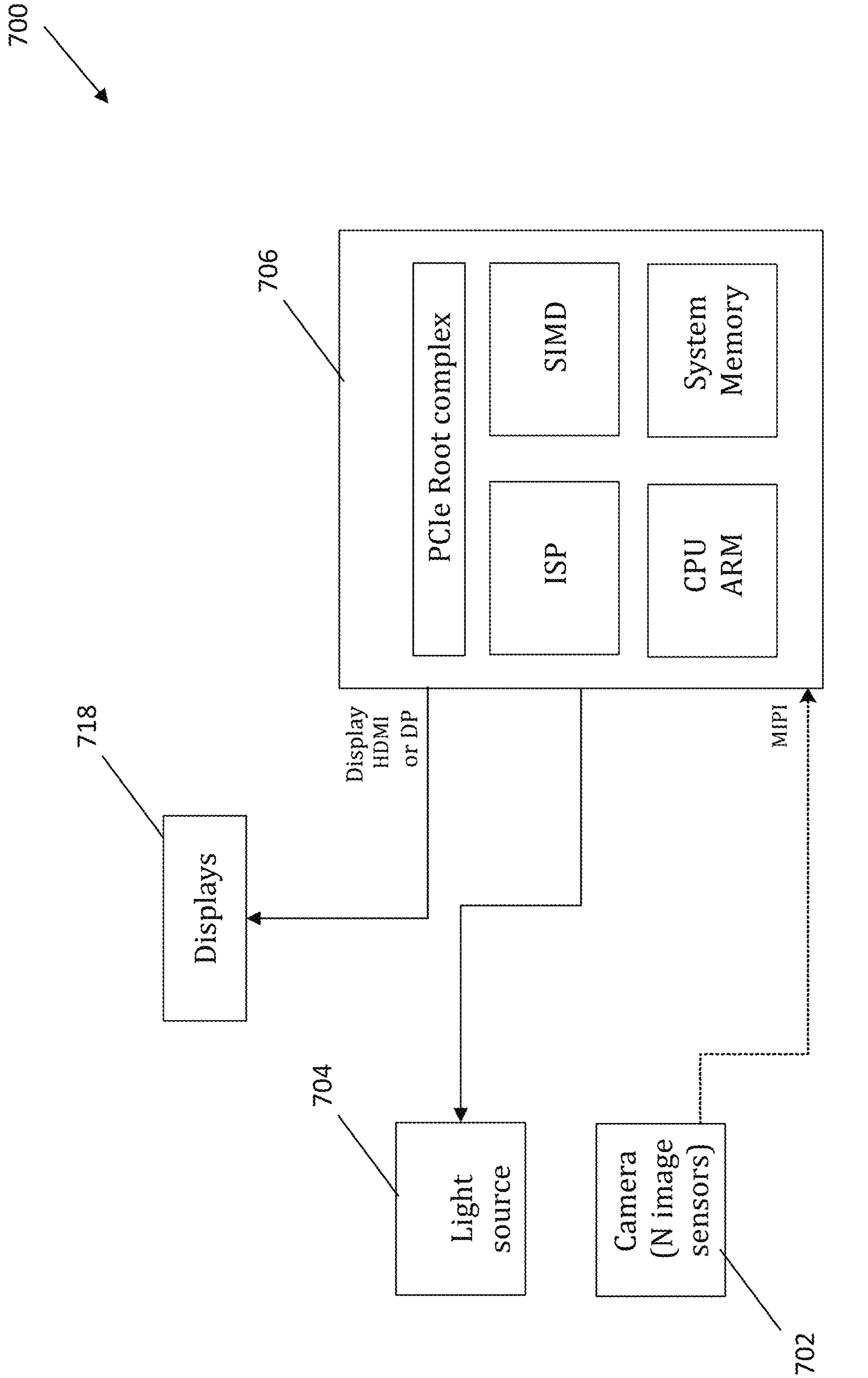
FIG. 7 illustrates another exemplary medical image processing system with SIMD processing capabilities according to examples of the disclosure.

An image processing unit utilizing a SIMD processor may not require an FPGA or other circuit to intervene between it and peripheral devices that send data to the processor, and to receive processed data from the SIMD processor. Instead, the embedded processor (of which the SIMD processor is a part of) can directly interface with any peripheral devices. FIG. 7 illustrates another exemplary medical image processing system with SIMD processing capabilities according to examples of the disclosure. In the example system 700 of FIG. 7, the light source 704, the camera 702, the displays 718 operate in substantially the same manner as the camera 302, light source 304, and displays 318 of FIG. 3, and thus a discussion of the operation of those components can be referenced above with respect to the discussion of their counterpart components of FIG. 3.

In one or more examples, the example system 700 includes an embedded processor 706 which includes the same components and functionality as processor 306 described above with respect to FIG. 3. However, in one or more examples, processor 706 can transmit processed image data directly to display 518 rather than transmitting the data to an FPGA. In one or more examples, the output images are converted by processor 706 to a format compatible with the display 718 using one or more display ports (not pictured) associated with the processor such as HDMI, DisplayPort, SDI, DVI or similar. Processor 706 can transmit the image data directly to the display 718 via OpenGL or similar interface. The processor 706 can be configured to also modify the output images with on-screen displays (OSD) or augmented reality overlays prior to transmitting the image to the display.

Processor 706 can also be configured to receive data directly from the camera 702 rather than requiring an intervening FPGA. The sensor data from camera 702 can be sent via MIPI CSI-2 (or any other image sensor protocol which is understood by the processor 706—referred as standard camera interface) to the processor 706. Thus, in contrast to the example of FIG. 3, no PCI express may be required for the receiving of the images. The infrastructure of the embedded processor 706 can be used to receive the image data from the standard camera interface and to save it into the frame buffer(s) found in the processor 706.

Figure 8:
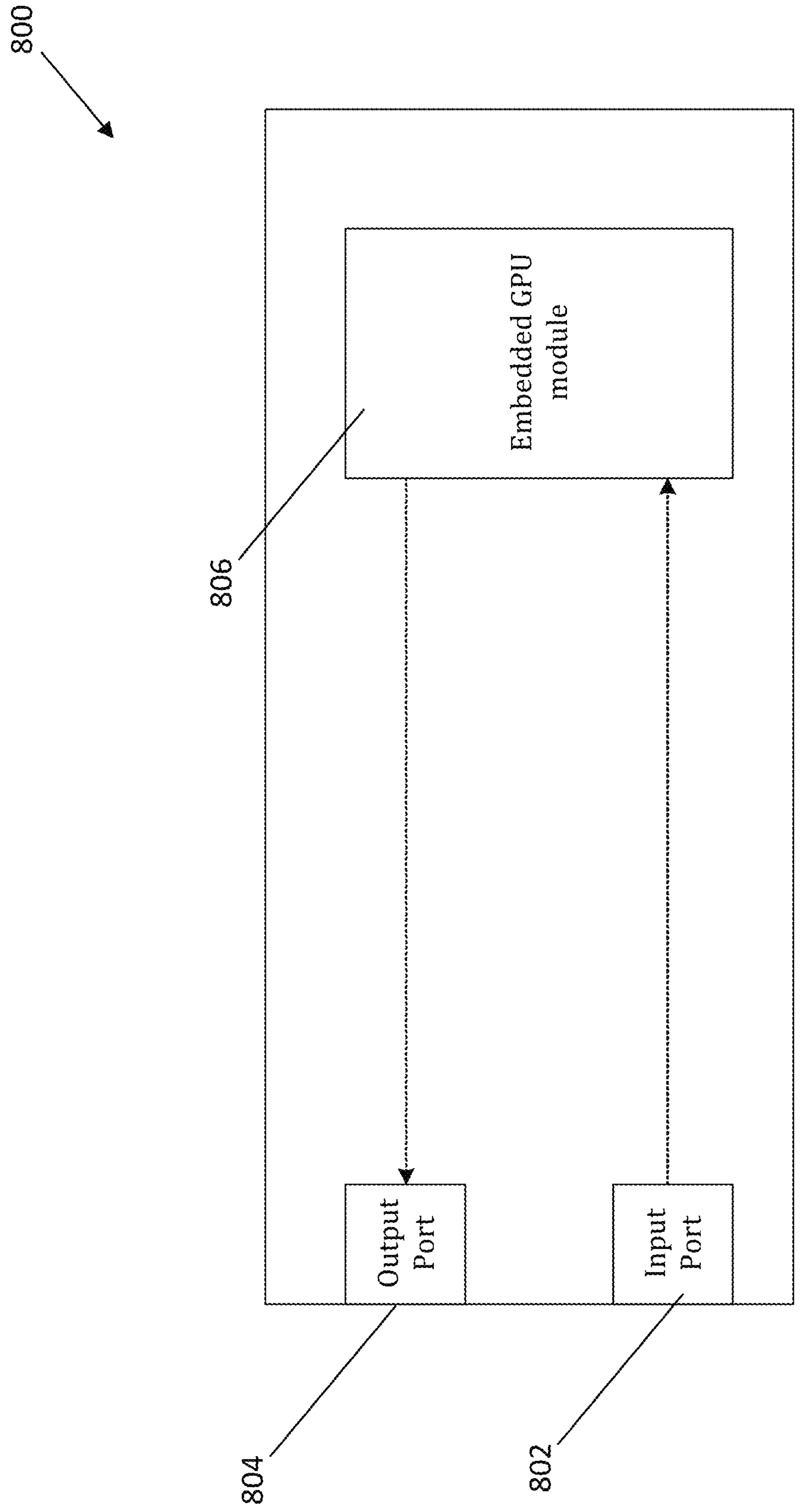
FIG. 8 illustrates another exemplary architecture for a medical image processing system according to examples of the disclosure.

FIG. 8 illustrates another exemplary architecture for a medical image processing system according to examples of the disclosure. The system architecture 800 of FIG. 8 can represent a simplified block diagram of the system 700 of FIG. 7 so as to better illustrate the main components of system 500 and their connections to one another.

The system architecture 800 of FIG. 8 can illustrate the layout of a chip board populated with the relevant components needed to implement the system. Architecture 800 can include input port 802 that is configured to receive image data from an image sensor (as described in detail above.) Embedded processor 806 (which represents processor 706 of FIG. 7) can be directly coupled to input port 802 and receive image data from an external camera that is connected to input port 802. The sensor data from a camera can be sent via MIPI CSI-2 (or any other image sensor protocol which is understood by the processor 806—referred as standard camera interface) to the processor 806. The infrastructure of the embedded processor 806 can be used to receive the image data from the standard camera interface and to save it into the frame buffer(s) found in the processor 806.

Processor 806 can transmit processed image data directly to a display that is connected to output port 804. In one or more examples, the output images are converted by processor 806 to a format compatible with the display connected to output port 804 using one or more display ports (not pictured) associated with the processor such as HDMI, DisplayPort, SDI, DVI or similar. Processor 806 can transmit the image data directly to the display via OpenGL or similar interface. The processor 806 can be configured to also modify the output images with on-screen displays (OSD) or augmented reality overlays prior to transmitting the image to the display.

Figure 9:
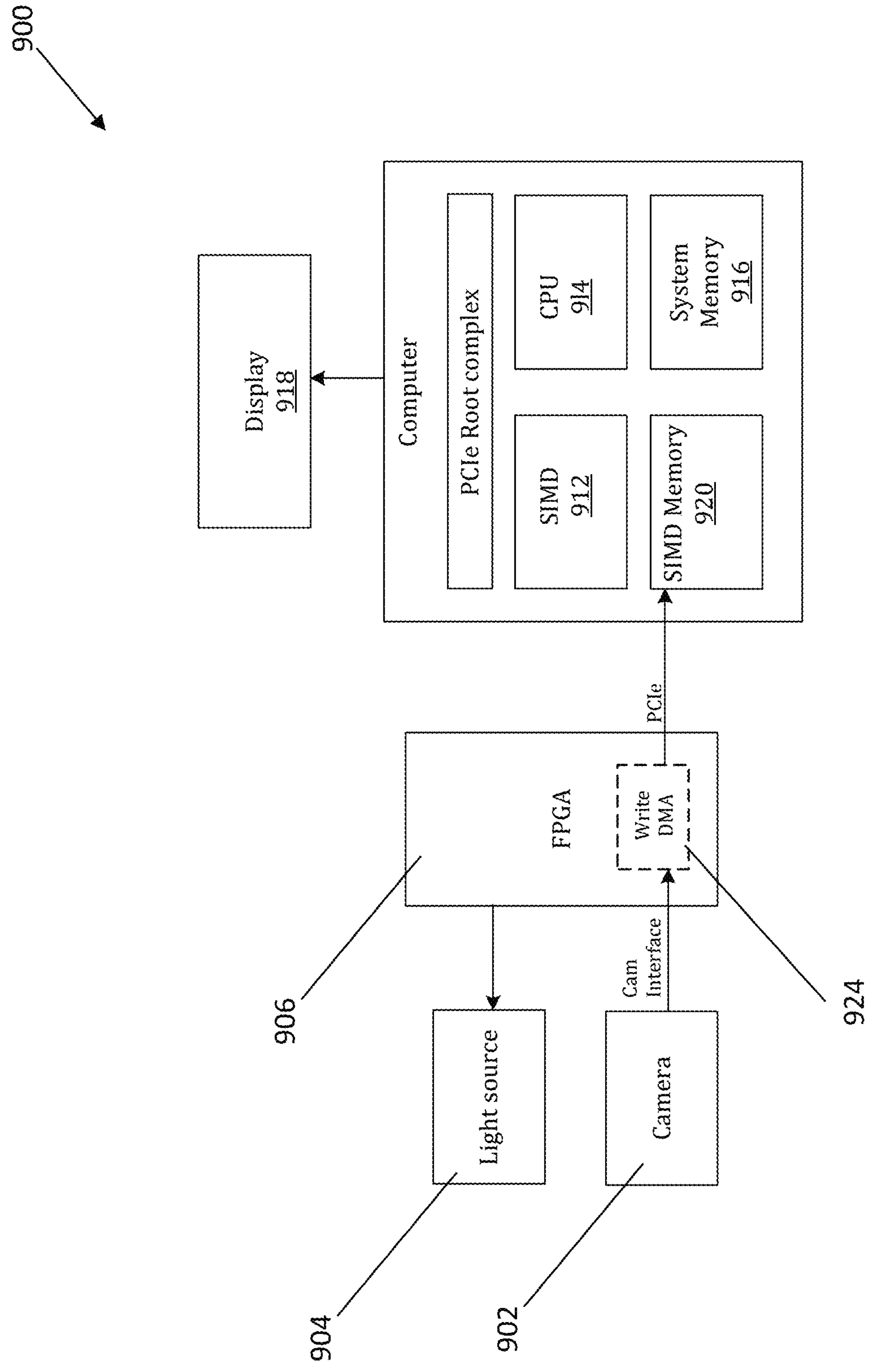
FIG. 9 illustrates another exemplary medical image processing system with SIMD processing capabilities according to examples of the disclosure.

FIG. 9 illustrates another exemplary medical image processing system with SIMD processing capabilities according to examples of the disclosure. The example system 900 of FIG. 9 can be substantially similar to the example of FIG. 5, except that rather than having processor 506 implemented as an embedded processor, the system 900 can instead implement the processor 906 using a desktop-like computer infrastructure with for instance an Intel x86/x64 based CPU 914 (as may be found in conventional desktop computing environments). The computer 906 can include a SIMD processor 912 that can be implemented using a GPU or other processor with a SIMD processing architecture. The FPGA 924 can include a write DMA 924 that can transfer received image sensor data directly into the SIMD processor memory 920. The CPU 914 can implement a Linux-based operating system which can be used to control SIMD processor 912 and generate the output to an OpenGL buffer which is shown onto the display 918. Camera 902, light source 904, FPGA 906, and write DMA 924 operate in substantially the same manner as their counterpart components described above with respect to FIGS. 3 and 5.

Figure 10:
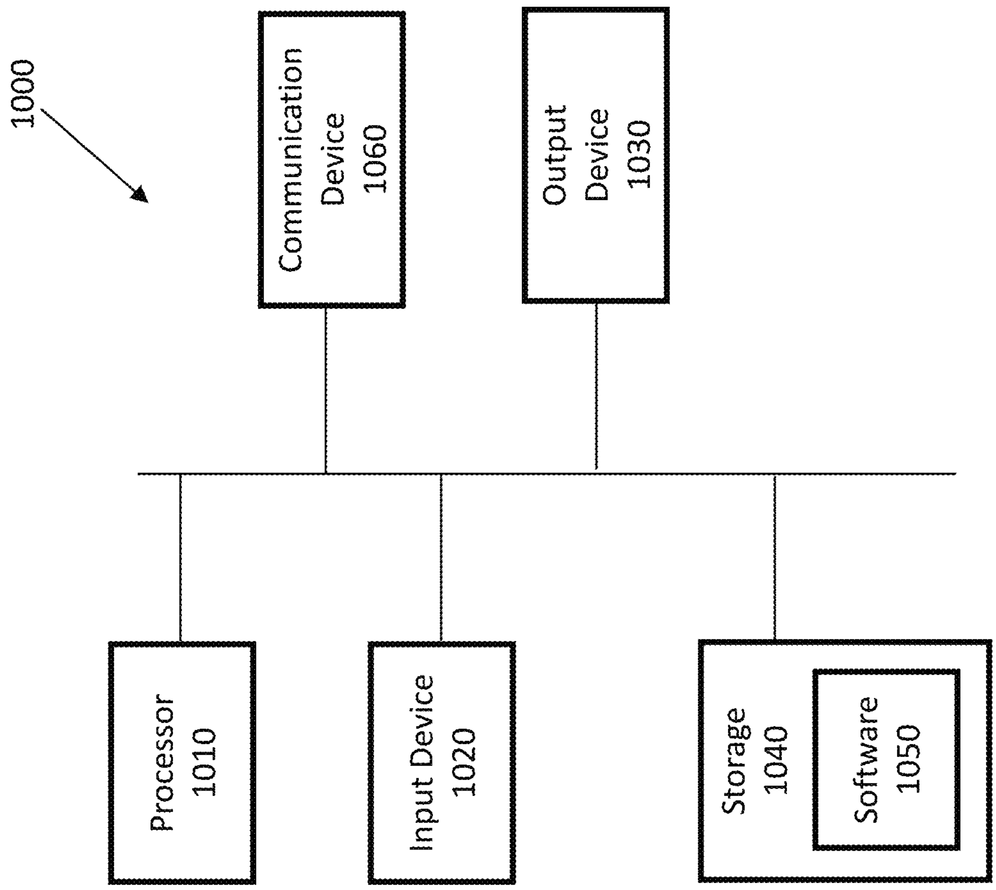
FIG. 10 illustrates an exemplary computing system, according to examples of the disclosure.

FIG. 10 illustrates an example of a computing system 1000, in accordance with some examples, that can be used for one or more of components of system 100 of FIG. 1, such as one or more of camera head 108, and camera control unit 112. System 1000 can be a computer connected to a network, such as one or more networks of hospital, including a local area network within a room of a medical facility and a network linking different portions of the medical facility. System 1000 can be a client or a server. As shown in FIG. 10, system 1000 can be any suitable type of processor-based system, such as a personal computer, workstation, server, handheld computing device (portable electronic device) such as a phone or tablet, or dedicated device. The system 1000 can include, for example, one or more of input device 1020, output device 1030, one or more processors 1010, storage 1040, and communication device 1060. Input device 1020 and output device 1030 can generally correspond to those described above and can either be connectable or integrated with the computer.

Input device 1020 can be any suitable device that provides input, such as a touch screen, keyboard or keypad, mouse, gesture recognition component of a virtual/augmented reality system, or voice-recognition device. Output device 1030 can be or include any suitable device that provides output, such as a display, touch screen, haptics device, virtual/augmented reality display, or speaker.

Storage 1040 can be any suitable device that provides storage, such as an electrical, magnetic, or optical memory including a RAM, cache, hard drive, removable storage disk, or other non-transitory computer readable medium. Communication device 1060 can include any suitable device capable of transmitting and receiving signals over a network, such as a network interface chip or device. The components of the computing system 1000 can be connected in any suitable manner, such as via a physical bus or wirelessly.

Processor(s) 1010 can be any suitable processor or combination of processors, including any of, or any combination of, a central processing unit (CPU), field programmable gate array (FPGA), and application-specific integrated circuit (ASIC). Software 1050, which can be stored in storage 1040 and executed by one or more processors 1010, can include, for example, the programming that embodies the functionality or portions of the functionality of the present disclosure (e.g., as embodied in the devices as described above)

Software 1050 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1040, that can contain or store programming for use by or in connection with an instruction execution system, apparatus, or device.

Software 1050 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport computer readable medium can include, but is not limited to, an electronic, magnetic, optical, electromagnetic, or infrared wired or wireless propagation medium.

System 1000 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, fiber optic lines, T1 or T3 lines, cable networks, DSL, or telephone lines.

System 1000 can implement any operating system suitable for operating on the network. Software 1050 can be written in any suitable programming language, such as C, C++, Java, or Python. In various example, application software embodying the functionality of the present disclosure can be deployed in different configurations, such as in a client/server arrangement or through a Web browser as a Web-based application or Web service, for example.

The foregoing description, for the purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated. For the purpose of clarity and a concise description, features are described herein as part of the same or separate examples; however, it will be appreciated that the scope of the disclosure includes examples having combinations of all or some of the features described.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A system for processing and displaying medical imaging data onto an electronic display, the system comprising:

a memory, wherein the memory is configured to be communicatively coupled to a medical imaging device, and wherein the memory is configured to:

receive one or more frames of video data from the medical imaging device, wherein each frame of the one or more frames comprises a plurality of data portions; and store the plurality of data portions of each frame of the received video data in one or more storage mediums of the memory;

a first processor, wherein the first processor is configured to:

access the plurality of data portions corresponding to a frame of the one or more frames from the memory;

process the plurality of data portions using a single instruction multiple data (SIMD) processing architecture such that each data portion of the plurality of data portions is separately processed in parallel using one or more common instructions; and transmit the processed plurality of data portions to an electronic display; and a second processor, wherein the second processor is communicatively coupled to the first processor, and wherein the second processor is configured to coordinate one or more operations of the first processor; and a third processor implementing a non-SIMD architecture, the third processor communicatively coupled to the medical imaging device, wherein the third processor is configured to:

receive the one or more frames of video data from the medical imaging device;

perform one or more image processing operations on at least a portion of the one or more frames; and transfer the one or more frames to the memory.

2. The system of claim 1, wherein transferring the one or more frames to the memory comprises converting each frame of the one or more frames of video data into a plurality of packets, wherein each packet includes a portion of the frame; and transferring the plurality of packets associated with each frame to the memory.

3. The system of claim 2, wherein the plurality of packets are Peripheral Component Interconnect Express (PCIe) packets.

4. The system of claim 2, wherein transferring the plurality of packets to the memory comprises performing a direct memory access (DMA) transfer.

5. The system of claim 4, wherein the DMA transfer is controlled by the third processor.

6. The system of claim 4, wherein the DMA transfer is controlled by the second processor.

7. The system of claim 2, wherein the third processor is configured to:

determine that one or more portions of the one or more frames has been received from the medical imaging device; and transmit a signal to the second processor when a determination has been made that the one or more portions of the one or more frames has been received from the medical imaging device.

8. The system of claim 7, wherein the second processor is configured to:

receive the signal from the third processor indicating that a complete frame of the one or more frames has been received from the medical imaging device; and cause the first processor to initiate processing the plurality of data portions upon receiving the signal from the third processor indicating that a complete frame of the one or more frames has been received from the medical imaging device.

9. The system of claim 7, wherein the first processor is configured to:

receive the signal from the third processor indicating that a complete frame of the one or more frames has been received from the medical imaging device; and initiate processing the plurality of data portions upon receiving the signal from the third processor indicating that a complete frame of the one or more frames has been received from the medical imaging device.

10. The system of claim 2, wherein the third processor is configured to receive one or more processed images from the first processor and is configured to perform the one or more image processing operations on the received one or more processed images.

11. The system of claim 2, wherein the third processor is configured to receive one or more processed images from the first processor using a direct memory access (DMA) transfer.

12. The system of claim 10, wherein the third processor comprises one or more output ports and is configured to output the received one or more processed images to the electronic display using the one or more output ports.

13. The system of claim 12, wherein the one or more output ports comprise high-definition multimedia interface (HDMI) output ports.

14. The system of claim 12, wherein the one or more output ports comprise DisplayPorts compatible output ports.

15. The system of claim 12, wherein the one or more output ports comprise Serial Digital Interface (SDI) output ports.

16. The system of claim 13, wherein the system comprises a multiplexer, wherein the multiplexer comprises:

a first input communicatively coupled to the output port of the third processor;

a second input of the multiplexer communicatively coupled to an output port of the first processor; and an output port communicatively coupled to the electronic display;

wherein the multiplexer is configured to select the first input or the second input to be transmitted to the electronic display using the output port based on one or more control signals received from the third processor.

17. The system of claim 2, wherein the third processor is configured to:

receive an image from the first processor to be overlaid on the one more received processed images from the first processor;

superimpose the received image onto the one or more received processed images to generate a composite image; and transmit the composite image to the electronic display.

18. The system of claim 2, wherein the third processor is a field programmable gate array (FPGA).

19. The system of claim 2, wherein the third processor is configured to be communicatively coupled to a light source, and wherein the integrated circuit is configured to operate the light source.

20. The system of claim 2, wherein the third processor is configured to determine if the first or second processor has failed and, if it is determined that the first or second processor has failed:

perform one or more image processing algorithms on the received one or more frames of video data to generate one or more processed frames of video data; and transmit the one or more processed frames of video data to the electronic display.

21. The system of claim 1, wherein the memory is configured to receive the one or more frames of video data in a mobile industry processor interface (MIPI) camera serial interface (format).

22. The system of claim 1, wherein the system comprises a fourth processor configured to perform one or more image signal processing algorithms on the received one or more frames of video data.

23. The system of claim 22, wherein the one or more image signal processing algorithms includes a de-mosaic algorithm.

24. The system of claim 22, wherein the one or more image signal processing algorithms includes a noise reduction algorithm.

25. The system of claim 1, wherein processing the plurality of data portions comprises applying one or more image signal processing algorithms selected from the group consisting of: Pixel defect correction, color leakage correction, de-mosaic, spatial and temporal noise reduction filters, sharpening filters, color space conversion, image stabilization, overlay of multiple image sensors, image augmentation, gamma correction, dewarping, and distortion correction.

26. The system of claim 1, wherein the second processor is configured to execute an operating system configured to manage operation of the first processor.

27. The system of claim 1, wherein the first processor is a graphics processing unit (GPU).

28. The system of claim 1, wherein the first processor is configured to be communicatively coupled to a light source, and wherein the first processor is configured to operate the light source.

29. The system of claim 1, wherein the second processor is configured to be communicatively coupled to a light source, and wherein the second processor is configured to operate the light source.

30. The system of claim 1, wherein processing the plurality of data portions comprises applying one or more artificial intelligence applications to the plurality of data portions.

31. The system of claim 30, wherein the first processor comprises one or more tensor cores configured to perform matrix operations.

32. The system of claim 31, wherein the one or more tensor cores are configured to apply the one or more artificial intelligence applications to the plurality of data portions.

33. The system of claim 1, wherein the memory is a buffer that is part of the first processor.

34. The system of claim 1, wherein the memory is a system memory shared by the first and second processors.

35. The system of claim 1, wherein the first processor is configured to perform one or more iterative algorithms on the plurality of data portions, wherein performing an iterative algorithm comprises:

applying a first common instruction to each data portion of the plurality of data portions to generate a plurality of first processed data portions;

storing each data portion of the plurality of first processed data portions in the memory; and applying a second common instruction to each data portion of the plurality of first processed data portions stored in the memory to generate a plurality of second processed data portions.

36. The system of claim 1, wherein the first processor is configured to perform video encoding on the received one or more frames of video data.

37. The system of claim 36, wherein performing video encoding on the received one or more frames comprises applying H.264 encoding on the received one or more frames of video data.

38. The system of claim 1, wherein the first processor is configured to perform one or more image processing algorithms on the received one or more frames of video data selected from the group consisting of pixel defect correction, color leakage correction, demosaicing, spatial filtering, temporal noise filtering, sharpening filtering, color space conversion, image stabilization, image augmentation, gamma correction, dewarping, image compression, image decompression, and distortion correction.

39. The system of claim 1, wherein the electronic display and the medical imaging device are operated using a common clock signal generated by the system.

40. A method for processing and displaying medical imaging data onto an electronic display, the method comprising, at a computing system:

accessing, by a first processor, a plurality of data portions stored in a memory, the plurality of data portions corresponding to a frame of one or more frames of video data from a medical imaging device;

processing, by the first processor, the plurality of data portions using a single instruction multiple data (SIMD) processing architecture such that each data portion of the plurality of data portions is separately processed in parallel using one or more common instructions;

transmitting, by the first processor, the processed plurality of data portions to an electronic display;

coordinating, by a second processor, one or more operations of the first processor;

receiving, by a third processor implementing a non-SIMD architecture, the one or more frames of video data from the medical imaging device;

performing, by the third processor, one or more image processing operations on at least a portion of the one or more frames; and transferring, by the third processor, the one or more frames to the memory.

* * * * *